(12) United States Patent
Centola (10) Patent No.: US 11,690,630 B2
(45) Date of Patent: Jul. 4, 2023

(54) OCCLUDER INSERTION SYSTEM (71) Applicant: QATNA MEDICAL GMBH, Hechingen (DE)

(72) Inventor: Marcos Centola, Hechingen-Stein (DE)

(73) Assignee: QATNA MEDICAL GMBH, Hechingen (DE)

(*) Notice: Subject to any disclaimer, the term of this patent is extended or adjusted under 35 U.S.C. 154(b) by 222 days.

(21) Appl. No.: 17/422,000

(22) PCT Filed: Jan. 9, 2020

(86) PCT No.: PCT/EP2020/050432
§ 371 (c)(1),
(2) Date: Jul. 9, 2021

(87) PCT Pub. No.: WO2020/144283
PCT Pub. Date: Jul. 16, 2020

(65) Prior Publication Data
US 2022/0096093 A1 Mar. 31, 2022

(30) Foreign Application Priority Data
Jan. 10, 2019 (DE) .................... 10 2019 100 531.0

(51) Int. Cl.
*A61B 17/12* (2006.01)
*A61B 17/00* (2006.01)
(52) U.S. Cl.
CPC .. *A61B 17/12122* (2013.01); *A61B 17/12172* (2013.01); *A61B 17/12177* (2013.01);
(Continued)
(58) Field of Classification Search
CPC ........ A61B 17/12122; A61B 17/12172; A61B 2017/00367; A61B 2017/12054
See application file for complete search history.

(56) References Cited

U.S. PATENT DOCUMENTS

| 5,201,757 A | 4/1993 | Heyn et al. |
| 2007/0135826 A1 | 6/2007 | Zaver et al. |

(Continued)

FOREIGN PATENT DOCUMENTS

| CN | 102895008 A | 1/2013 |
| DE | 102009020012 A1 | 11/2010 |

(Continued)

OTHER PUBLICATIONS

International Search Report Form PCT/ISA/210, and Written Opinion Form PCT/ISA/237, International Application No. PCT/EP2020/050432, pp. 1-14 International Filing Date Jan. 9, 2020 dated Mar. 25, 2020.

(Continued)

*Primary Examiner* — Sarah A Simpson
*Assistant Examiner* — Raihan R Khandker
(74) *Attorney, Agent, or Firm* — George McGuire (57) ABSTRACT

System for inserting a self-expandable occluder (12) into a patient and for releasing the occluder (12) in the left atrial appendage (10) of the patient, the system including an insertion unit (100) which has a drive unit (102) and an insertion catheter including an outer tube and an inner tube extending through the outer tube, wherein a proximal end region of the occluder is movement-coupled to the outer tube, and wherein a distal end region of the occluder, is movement-coupled to the inner tube, wherein, in order to release the occluder, the drive unit interacts with the inner tube and the outer tube such that, when actuated, the inner tube can be moved in a distal or proximal direction and the outer tube can be moved in the proximal direction or distal direction, so that the distal end and the proximal end of the occluder can be moved away from or toward one another.

17 Claims, 9 Drawing Sheets (52) U.S. Cl.
CPC ............... *A61B 2017/00367* (2013.01); *A61B 2017/12054* (2013.01)

(56) References Cited

U.S. PATENT DOCUMENTS

| | | |
|---|---|---|
| 2007/0167981 A1 | 7/2007 | Opolski et al. |
| 2009/0088795 A1 | 4/2009 | Cahill |
| 2010/0114128 A1 | 5/2010 | Coleman et al. |
| 2012/0185031 A1 | 7/2012 | Ryan |
| 2013/0144276 A1* | 6/2013 | Crisostomo ........... A61F 2/2436 606/1 |
| 2014/0121755 A1 | 5/2014 | Farag et al. |
| 2017/0056222 A1* | 3/2017 | Bradway ................. A61F 2/954 |

FOREIGN PATENT DOCUMENTS

| | | |
|---|---|---|
| EP | 1523957 A2 | 4/2005 |
| EP | 2266465 A1 | 12/2010 |
| JP | 2003529410 A | 10/2003 |
| JP | 2008514291 A | 5/2008 |
| WO | 2006036837 A2 | 4/2006 |
| WO | 2007098232 A2 | 8/2007 |
| WO | 2010127838 A2 | 11/2010 |
| WO | 2015079023 A1 | 6/2015 |
| WO | 2017157316 A1 | 9/2017 |

OTHER PUBLICATIONS

German Exam Report, dated Oct. 14, 2019, pp. 1-4.
Mon English Translated Search Report, dated Dec. 8, 2022, pp. 1-16.
Mon-translated JP Office Action, dated Jan. 31, 2023. pp. 1-2.
Translated Chinese Office Communication, dated Jan. 20, 2023, Application No. 2022109535730, pp. 1-4.

* cited by examiner

OCCLUDER INSERTION SYSTEM

CROSS-REFERENCE TO RELATED APPLICATIONS

This is a National Stage Application filed under 35 U.S.C. 371 based on International Patent Application No. PCT/EP2020/050432, filed on Jan. 9, 2020, which claims priority to German Patent Application No. 10 2019 100 531.0 filed on Jan. 10, 2019, the disclosures of both of which are incorporated herein by reference in their entireties.

The invention relates to a system for inserting a self-expandable occluder into a patient and for releasing the occluder in the left atrial appendage (auricula cordis sinistra) of the patient.

The auriculae atrii or atrial appendages are protuberances of the atria of the heart in mammals. The left atrial appendage (LAA), known medically as the auricula cordis sinistra, is located next to the pulmonary artery tract and is a frequent site for blood clots that can lead to a stroke, especially in patients with atrial fibrillation. Preventing thrombi in the left atrial appendage is therefore an effective stroke prophylaxis in vulnerable patients.

For this stroke prophylaxis, implants have been developed that are introduced into the protuberances and close the access, for example using a Teflon film. These implants are referred to as LAA (left atrial appendage) occluders. These implants are inserted into the protuberances and anchored there in particular by means of anchoring elements, so that, in particular via the proximal end region thereof, they close off the access into the protuberances in a fluid-tight manner. Insertion mostly takes place using endovascular techniques, i.e. in particular by means of an insertion catheter through which the implant is brought to the place of use. The occluders are brought to the place of use in particular in a reduced-volume form, and expanded there. Self-expanding materials are generally used for the occluders, for example shape-memory alloys. An occluder of this kind is previously known from WO 2015/079023 A1.

It is known to use a guide wire to insert an occluder into the left atrial appendage of a patient. The guide wire, as disclosed for example in WO 2015/079023 A1, is screwed tightly to an internal thread of the occluder by means of an external thread. The occluder is then brought to its intended position in the region of the left atrial appendage. Once the occluder has assumed its self-expanded shape at its intended location, the guide wire can be detached from the occluder by unscrewing the guide wire from the occluder. An occluder of this kind is also disclosed in WO 2006/036837 A2, wherein the occluder is formed in two parts and is provided for closing an atrial septal defect. In this process, undesirable torques can act on the occluder in particular and, in the worst case, even lead to the occluder becoming detached from its intended position. There is therefore a need to rectify these disadvantages.

There is also a need to be able to move an occluder as easily as possible into an insertion position, which can in particular be a compressed position, in order to bring the occluder to the left atrial appendage in this insertion position.

It is also known from DE 10 2009 020 012 A1 and U.S. Pat. No. 5,201,757 that a stent can be brought into its self-expanded shape by moving two elements of a catheter in opposite directions. In US 2012/185031 A1, an insertion system for a stent is also disclosed, wherein a drive element for expanding the stent is arranged on a handle.

EP 2 266 465 A1 discloses an occlusion instrument wherein no parts protrude beyond the proximal end of the occlusion instrument during insertion.

A handling unit for inserting a prosthesis is known from US 2017/0056222 A1, wherein two elements of the handling unit can be rotated relative to one another such that an outer tube and an inner tube move in translation relative to one another and the shape expands from the gap that forms.

WO 2017/157316 A1 also discloses an insertion catheter for inserting an occluder, wherein the occluder is folded into an insertion position.

Overall, the problem addressed by the present invention is therefore that of developing the known prior art.

This problem is solved by a system having the features of claim 1.

A system is accordingly proposed for inserting a self-expandable occluder into a patient and for releasing the occluder in the left atrial appendage of the patient. The system comprises an insertion unit which has a drive unit and has an insertion catheter comprising an outer tube and an inner tube extending through the outer tube. A proximal end region of the occluder is movement-coupled to the outer tube, while a distal end region of the occluder is movement-coupled to the inner tube. The drive unit interacts with the inner tube and the outer tube of the occluder in such a way that, when actuated, the inner tube can be moved in a distal or proximal direction and the outer tube can be moved in the proximal or distal direction, so that the proximal end and the distal end of the occluder can be moved away from or toward one another.

Movement-coupling the proximal end region of the occluder to the outer tube and the distal end region of the occluder to the inner tube means that the proximal end and the distal end of the occluder can be moved away from or toward one another. In order to insert the occluder into a patient and guide the occluder to the left atrial appendage, the inner tube can therefore first be moved in the distal direction, while the outer tube is moved in the proximal direction. In so doing, the proximal end and the distal end of the occluder can be moved away from one another in order to bring the occluder into an insertion position. In this insertion position, the occluder is accordingly arranged in a compressed form, so that it has an increased length but a reduced diameter. As a result, it can be brought to the left atrial appendage through blood vessels in particular.

By contrast, in order to release the occluder in the left atrial appendage, the inner tube can be moved in the proximal direction, while the outer tube can be moved in the distal direction. In so doing, the proximal end and the distal end of the occluder move toward one another, with the occluder developing in particular into its self-expanded shape. In so doing, the length of the occluder is reduced while its diameter increases. During this release process, the occluder comes to rest against the left atrial appendage, in order to thus close the left atrial appendage by means of the occluder.

Overall, the position of the occluder can be changed in a particularly simple manner, in order to transfer the occluder into an insertion position in which the occluder can be brought to the left atrial appendage of a patient in a particularly simple manner, and in order to be able to release the occluder, the occluder developing in particular into its self-expanded shape and, after release, tightly closing the left atrial appendage.

The drive unit also has a first transmission element that has a first transmission thread, a second transmission element that has a second transmission thread, and an actuating element that can be actuated by an operator and has a first drive thread and a second drive thread. The first transmission element is in this case movement-coupled to the inner tube. The second transmission element is movement-coupled to the outer tube. The first drive thread interacts with the first transmission thread, while the second drive thread interacts with the second transmission thread, in order to move the distal ends of the outer tube and the inner tube toward or away from one another. Movement coupling between the drive unit and the outer tube or inner tube of the insertion catheter can thereby be provided in a particularly simple manner. The first and the second drive thread can be formed as one piece. In particular, the actuating element can be formed as one piece overall. When the actuating element is actuated, the distal ends of the outer tube and the inner tube can consequently be moved toward or away from one another at the same time. The first transmission thread and the second transmission thread can be synchronous and the first drive thread and the second drive thread can be synchronous, such that when the actuating element is actuated, the inner tube and the outer tube are each moved in opposite directions by the same distance.

The first drive thread is also designed as a first internal or external thread which interacts with the first transmission thread which is designed as an external or internal thread. Furthermore, the second drive thread is advantageously designed as a second internal or external thread which interacts with the second transmission thread which is designed as an external or internal thread. The first and the second drive thread can be formed as one piece with one another. Overall, a movement coupling and a synchronous movement in opposite directions can be achieved thereby in a particularly simple manner.

In an advantageous development of the invention, the outer tube ends in front of the inner tube in the distal direction. As a result, the proximal end region of the occluder can be movement-coupled to the outer tube and the distal end region of the occluder can be movement-coupled to the inner tube in a particularly simple manner.

In a further advantageous embodiment of the invention, the occluder comprises a frame that has a tubular proximal end region through which the insertion catheter is inserted into the occluder. In this way, the insertion catheter can be inserted into the occluder in a particularly simple manner. The distal end of the outer tube can in this case be located directly after the tubular proximal end region in the distal direction, so that the outer tube interacts in particular with the tubular proximal end region of the occluder for the purpose of movement coupling. It is conceivable for the outer tube to interact with the tubular proximal end portion in a form-fitting or force-fitting manner. Furthermore, the occluder develops in particular into its self-expanded shape so that, from the insertion position, when the outer tube moves in the distal direction, the occluder can support the movement by intrinsically developing into the expanded position.

It is also advantageous for the occluder to comprise a pot-shaped distal end region on which the inner tube of the insertion catheter is arranged. The distal end region of the inner tube can consequently be inserted in particular into the pot-shaped distal end region of the occluder and end therein. The pot-shaped distal end region therefore comprises in particular a circular-cylindrical sheath portion and a base portion. Consequently, movement coupling between the inner tube and the distal end region of the occluder can be provided in particular in the distal direction. It is conceivable for the inner tube to be arranged in the distal pot-shaped end region in a form-fitting or force-fitting manner. As a result, movement coupling between the inner tube and the distal pot-shaped end region of the occluder can also be provided when the inner tube is moved in the proximal direction. Furthermore, the occluder develops in particular into its self-expanded shape so that, from the insertion position, when the inner tube moves in the proximal direction, the occluder can support the movement by intrinsically developing into the expanded position.

It is particularly preferred if, in order to be inserted into a patient, the occluder can be moved into an insertion position by a distal end of the inner tube and a distal end of the outer tube being moved relative to one another and away from one another, so that the proximal end and the distal end of the occluder can be moved away from one another. In this insertion position, the occluder can in particular have a reduced diameter and can thus be compressed. In this case the occluder can have an increased length, and therefore, in the insertion position, the occluder has a reduced diameter but a greater length by comparison with the release position. In this insertion position, the occluder can be brought up to the left atrial appendage particularly easily.

It is particularly preferred if, in order to release the occluder, the distal ends of the inner tube and the outer tube can be moved toward one another in such a way that the proximal end and the distal end of the occluder can be moved toward one another. In particular, it is conceivable that, during the release process, the occluder develops in particular into its self-expanded shape so that, from the insertion position, when the inner tube moves in the proximal direction or the outer tube moves in the distal direction, the occluder intrinsically develops into the expanded position.

In this case, a central part of the occluder between the proximal end and the distal end can keep its position substantially unchanged during the release of the occluder. In order to release the occluder at its intended position in the region of the left atrial appendage, the distal ends of the inner tube and the outer tube are consequently moved toward one another, so that the proximal end and the distal end of the occluder also move toward one another. Because the occluder can in particular be self-expanding, the occluder can in particular develop into its self-expanded position during the release process. In the end position, the occluder can come to rest against the inside of the left atrial appendage and tightly close the left atrial appendage, in order to reduce the risk of thrombus formation and the risk of stroke associated therewith. In the end position, the occluder can adopt its self-expanding final shape. However, it is also conceivable that the end position of the occluder, in which it rests tightly against the left atrial appendage, is already reached before the self-expanded final shape is reached, and then the occluder cannot deform any further.

It is conceivable that the occluder has a central axis which extends through the proximal end region and the distal end region. The occluder can extend around this axis. In the insertion position, the occluder can have a center point along this axis between the proximal end and the distal end. When the occluder is then released, in particular the proximal end and the distal end of the occluder can be moved toward one another in such a way that the center point of the occluder maintains or substantially maintains its position. This makes it possible to arrange and release the occluder on the left atrial appendage in a particularly precisely positioned manner. In its end position, the occluder can in particular have a spherical outer contour, so that the center point can also be the center point of the circular outer contour.

The outer tube preferably has, at its distal end region, at least one latching finger-like portion, in particular two or more, which interacts with the proximal end region of the occluder for the purpose of movement coupling. A particularly simple movement coupling can be achieved in this manner. In this case, the latching finger-like portion can interact in particular with the tubular proximal end portion of the occluder and engage behind it in particular for the purpose of movement coupling during a movement in the proximal direction. The outer tube can in particular be formed as one piece.

In a particularly preferred development of the invention, the first transmission element interacts with a Luer connector arranged on the inner tube for the purpose of movement coupling to the inner tube. A Luer connector can therefore be arranged on the inner tube. This connector can be arranged, for example, on the first transmission element for the purpose of movement coupling.

In a particularly preferred development of the invention, the latching finger-like portion is arranged on the proximal end region of the occluder in a form-fitting manner when the inner tube is arranged in the occluder. In particular, the latching finger-like portion can be elastically yielding and, starting from a rest position, can be deflected out of this rest position after the inner tube is inserted through the outer tube. When the inner tube is then passed through the outer tube, the latching finger-like portion cannot deflect radially inward and thus a stable form-fit between the proximal end region of the occluder and the latching finger-like portion can be established.

It is particularly preferred if, in order to remove the insertion catheter from the occluder, the inner tube can first be pulled out of the occluder. As soon as the inner tube is pulled out of the occluder through the outer tube, the outer tube can then be pulled out of the occluder.

The form-fitting connection between the outer tube and the proximal end region of the occluder can therefore only be broken when the inner tube has been pulled out of the occluder through the outer tube. As stated above, in order to release the occluder, the distal end and the proximal end of the occluder can consequently be moved toward one another by means of the outer tube and the inner tube, by the distal ends of the outer tube and the inner tube being moved toward one another. In so doing, the occluder pushes into its self-expanded shape.

As soon as this process of moving the proximal and distal ends of the occluder toward one another is completed, the insertion catheter can be pulled off the occluder in a particularly simple manner by first pulling the inner tube out of the occluder through the outer tube. The outer tube can then be pulled out of the occluder, wherein in particular the latching finger-like portion at the distal end region of the outer tube can be moved elastically inward in the radial direction in order to pull the outer tube out of the in particular tubular proximal end portion of the occluder.

As a result of this process, undesired torque transmission from the insertion catheter to the occluder can therefore be substantially completely or in particular completely prevented. This can minimize or eliminate the risk of the occluder being released from its intended position on the left atrial appendage when the insertion catheter is removed from the occluder. After the insertion catheter has been removed, the occluder can push completely into its self-expanded shape and, in particular, close the left atrial appendage in a completely fluid-tight manner.

The insertion unit advantageously has a housing which can be held by an operator, wherein the transmission elements and the actuating element are arranged in or on the housing. An operator, for example a surgeon, can accordingly hold the housing in their hand, and therefore the housing can be designed in the manner of a handle. The transmission elements and/or the actuating element can be arranged in or on the housing.

The actuating element is preferably rotatably arranged on the housing. The housing can have a central longitudinal axis and the actuating element can be rotated about the central longitudinal axis. The actuating element can in particular be formed as one piece, and in particular be hollow-cylindrical and have an internal thread.

The problem stated at the outset is also solved by an insertion unit for a system according to the invention. Accordingly, the insertion unit comprises a drive unit and an insertion catheter comprising an outer tube and an inner tube extending through the outer tube. By means of the insertion catheter, an occluder can be moved into an insertion position in a particularly simple manner, in order to be supplied to the left atrial appendage. The occluder can then be transferred into its end position by means of the insertion unit in order to close the left atrial appendage. Finally, the insertion catheter can be pulled off the occluder in a particularly simple manner, in particular without a substantial torque being transmitted to the occluder. As a result, the occluder can be positioned on the left atrial appendage in a more reliable and more secure manner.

Further details and advantageous embodiments of the invention can be found in the following description, on the basis of which the embodiment of the invention shown in the figures is described and explained in more detail. In the drawings.

Figure 1:
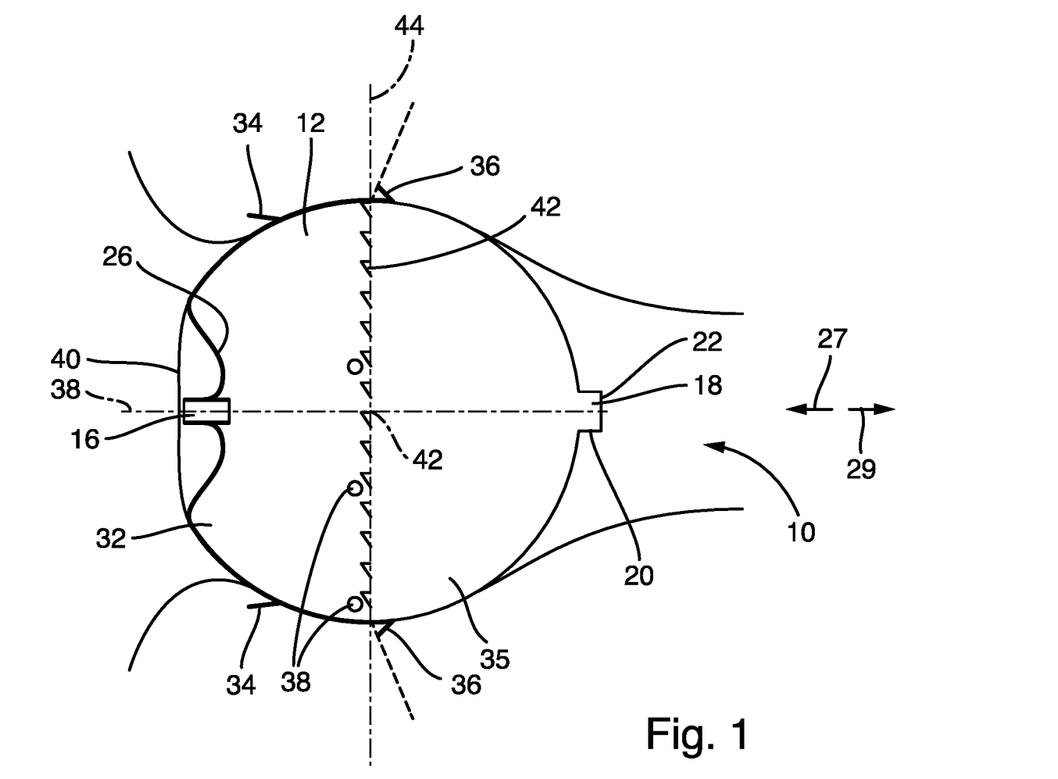
FIG. 1 is a schematic plan view of an occluder according to an embodiment that is arranged on the left atrial appendage.

Firstly, FIG. 1 schematically shows the left atrial appendage of a patient, denoted with reference sign 10. To reduce the risk of a stroke, an occluder 12 is introduced into the left atrial appendage 10 in order to close the access to the left atrial appendage 10.

Figure 4:
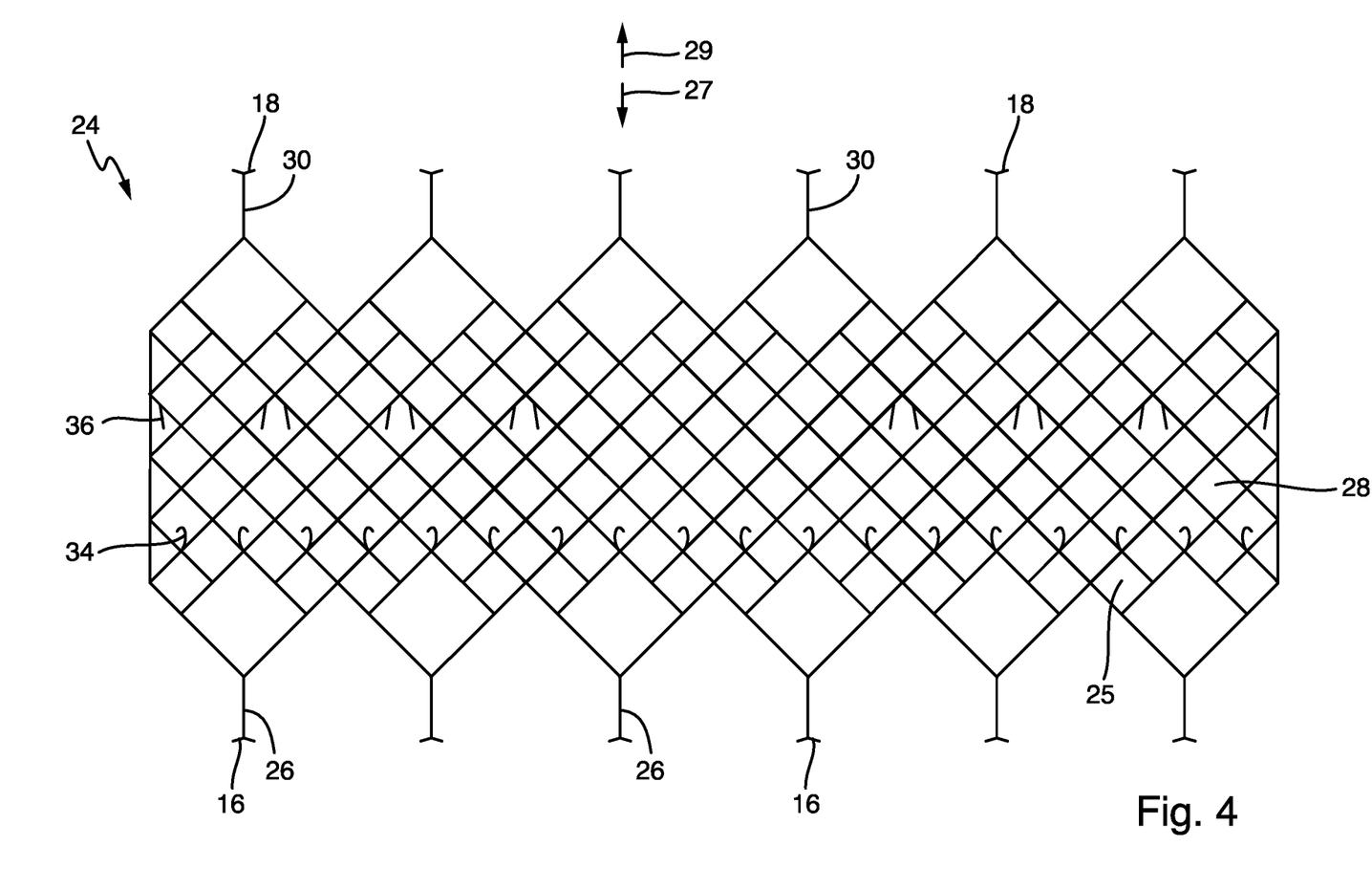
FIG. 4 is a cutaway schematic view of a frame portion of the occluder according to FIG. 2.

The occluder 12 initially comprises a frame 14 formed as one piece. This frame comprises a proximal tubular portion 16 and a pot-shaped distal end portion 18. The pot-shaped distal end portion 18 comprises a circular-cylindrical sheath portion 20 and a base portion 22, in order to form a pot-shaped structure. The occluder has a net-like frame portion 24 between the two end portions 16, 18. This net-like frame portion 24 can be seen particularly clearly in a cut-open form in FIG. 4. Starting from the proximal tubular end portion 16, the net-like frame portion 24 initially has a number of webs 26. These merge into a branching network of webs 25 in order to form the net structure. In so doing, diamond-shaped structures 28 are formed. In the distal direction 29, the webs 25 converge again into individual webs 30 which open into the distal end portion 18.

In the arranged state (cf. FIG. 1), the occluder 12 has a proximal hemisphere 32 and a distal hemisphere 35. A number of first anchoring means 34 are provided in the region of the proximal hemisphere 32. These extend along a circular line along the circumference and are in the form of hooks having end portions pointing in the proximal direction 27. Second anchoring means 36 are formed in the region of the distal hemisphere 35. These likewise extend along a circular line along the circumference, have a rod-like shape and protrude obliquely from the circumferential surface in the proximal direction 27. The anchoring means 34, 36 are also formed as one piece with the frame 14.

The frame 14 of the occluder 12 consists of a self-expanding material, for example a shape-memory alloy, in particular a nitinol alloy. The expanded shape impressed on the occluder 12 is spherical (cf. FIG. 2). The occluder 12 has a longitudinal axis 38 extending in the proximal or distal direction through its center point. This longitudinal axis 38 also extends through the central longitudinal axis of the tubular proximal end portion 16 and through the central longitudinal axis of the distal end portion 18 (cf. FIG. 2). The proximal hemisphere 32 is completely covered by a biological tissue 40. This biological tissue 40 is in particular a biological membrane. In particular, it can be the pericardium membrane. The tissue 40 comprises openings, such that the first anchoring means 34 protrude through the openings. The tissue 40 also has an insertion opening in order to insert an insertion catheter through the proximal tube portion 16 into the occluder 12. When the insertion catheter has been removed from the occluder 12 after the occluder 12 has been released, the elastically yielding tissue 40 can contract in such a way that the insertion opening is closed in a substantially fluid-tight manner, so that overall the tissue 40 closes off the proximal hemisphere 32 in a substantially fluid-tight manner and substantially covers the frame 14. As indicated schematically by surgical threads 42, the tissue is sewn to the frame 14 by means of PTFE threads.

In the vicinity of the parting plane 44 of the proximal hemisphere 32 and the distal hemisphere 35, a number of X-ray markers 38 are placed over the circumference in the region of the proximal hemisphere 32. These allow the occluder 12 to be precisely positioned in the left atrial appendage. A surgeon can consequently place the occluder 12 in a particularly precisely positioned manner.

Overall, by providing the biological tissue 40, an occluder 12 that has comparatively high biocompatibility can be provided. In this case, after the occluder 12 has been arranged on the left atrial appendage, the patient's natural tissue can grow over the biological tissue 40. As a result of the biological tissue 40 used, there is overall high biocompatibility and thus an increased probability that surgical intervention to close the left atrial appendage is successful.

Figure 5:
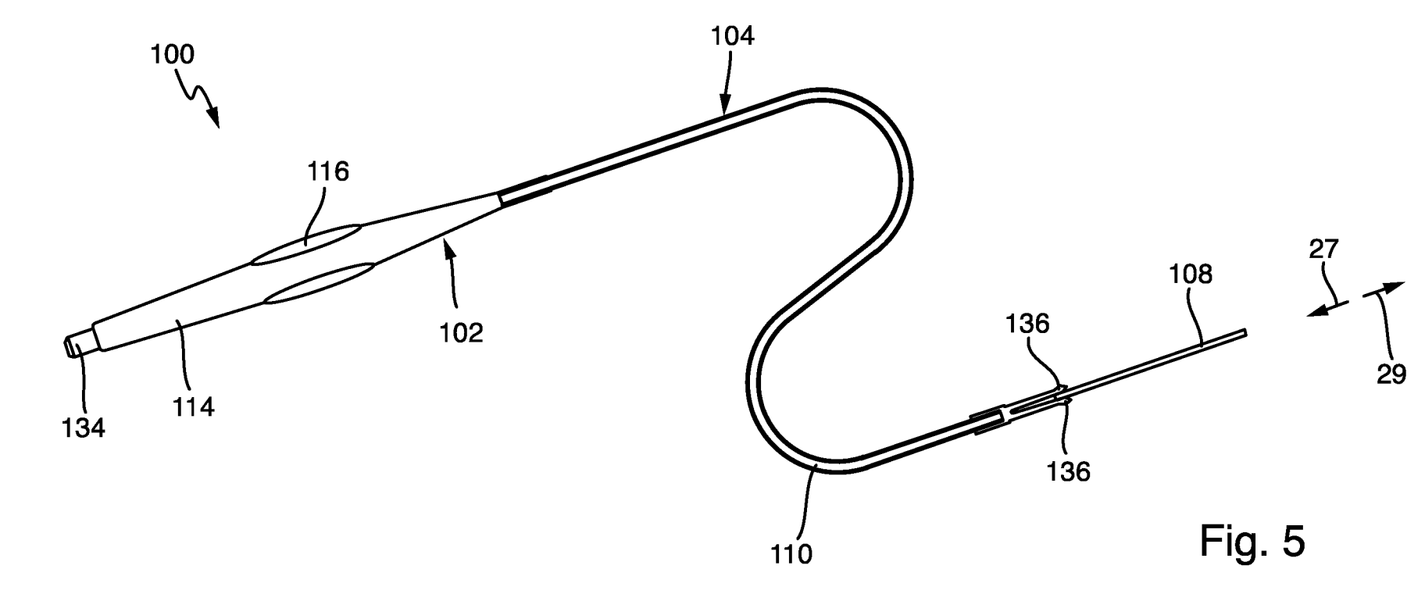
FIG. 5 is a perspective schematic view of an insertion unit according to an embodiment.

In the following, a system for inserting the occluder 12 into a patient and for releasing the occluder 12 in the left atrial appendage 10 of the patient is described according to one embodiment:

FIG. 5 shows an insertion unit 100 as a whole. This comprises both a drive unit 102 and an insertion catheter 104. The insertion catheter 104 comprises an inner tube 108 and an outer tube 110. The inner tube 108 extends through the outer tube 110. Moreover, the outer tube 110 ends in front of the inner tube 108 in the distal direction 29. The drive unit 102 comprises a housing 114 which can be held in the hand of an operator, in particular a surgeon, and which overall has an elongate shape.

The drive unit 102 also comprises an actuating element 116 which is rotatably arranged in the housing 114. The actuating element 116 is hollow and has a first drive thread 118 and a second drive thread 120, the first drive thread 118 being proximal to the second drive thread 120 (cf. FIGS. 6 and 7). The actuating element 116 is in particular formed as one piece.

A first transmission element 122 and a second transmission element 124 are also arranged in the housing 114. The two transmission elements 122, 124 overall have a helical shape. The first transmission element 122 has a thread portion 126 and a head portion 128. The second transmission element 124 correspondingly has a thread portion 130 and a head portion 132. The two transmission elements 122, 124 can in particular each be formed as one piece. The first transmission element 122 is in this case movement-coupled to the inner tube 108, while the second transmission element 124 is movement-coupled to the outer tube 110. The head portion 128 of the first transmission element 122 interacts with a Luer connector 134 that is fastened to the inner tube 108. The Luer connector 134 is detachably arranged on the head portion 128 of the first transmission element 122.

The head portion 132 of the second transmission element 124 interacts with the outer tube 110 for the purpose of movement coupling. The outer tube 110 is detachably arranged on the head portion 132.

Figure 9:
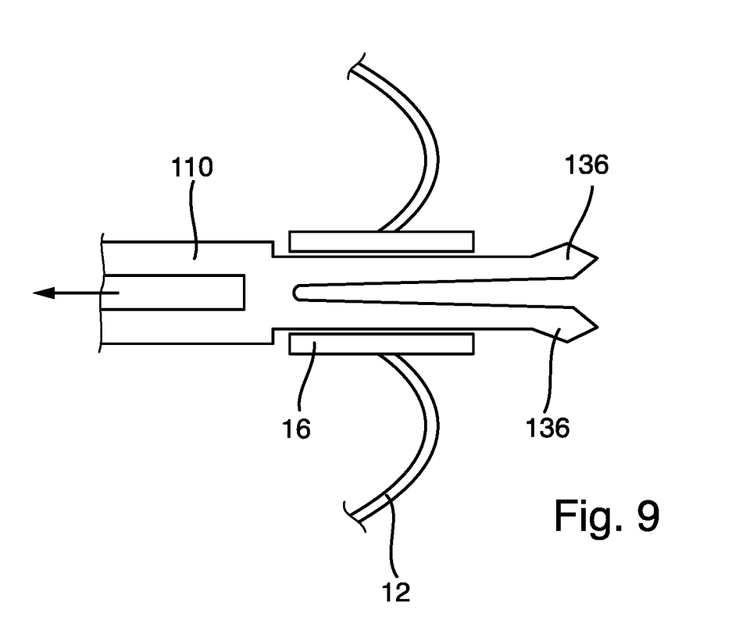
FIG. 9 is a view based on FIG. 8, with the inner tube of the insertion unit removed from the occluder.

At the distal end of the outer tube 110, said tube has two latching finger-like end portions 136, which can be seen particularly clearly in FIG. 9. These are formed as one piece with the outer tube 110 and can be deformed in an elastically yielding manner. Overall, the mode of operation of the insertion unit 100 is then as follows:

In order to insert the occluder 12 into the left atrial appendage 10, the insertion catheter 104 is firstly arranged on the occluder 12 in order to form a system consisting of the insertion unit 100 and occluder 12, in order to bring the occluder 12 to the left atrial appendage 10 and then release the occluder 12.

Figure 2:
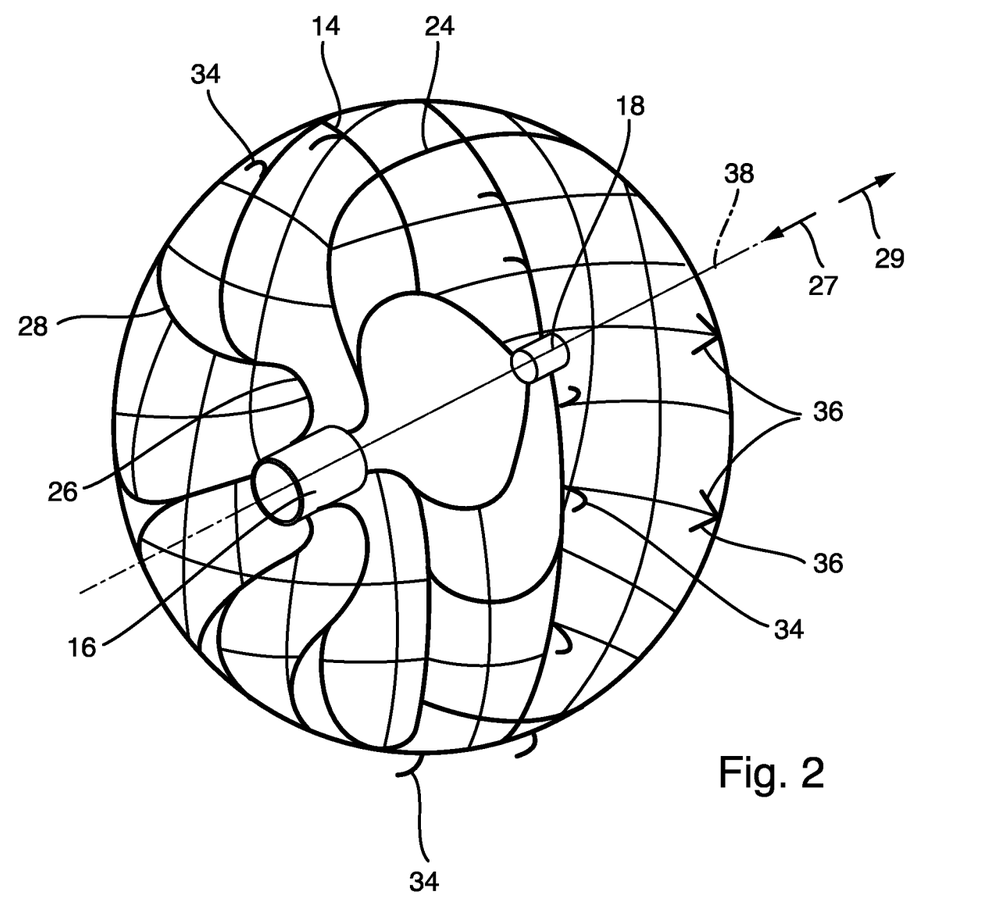
FIG. 2 is a schematic perspective view of the occluder according to FIG. 1.
Figure 3:
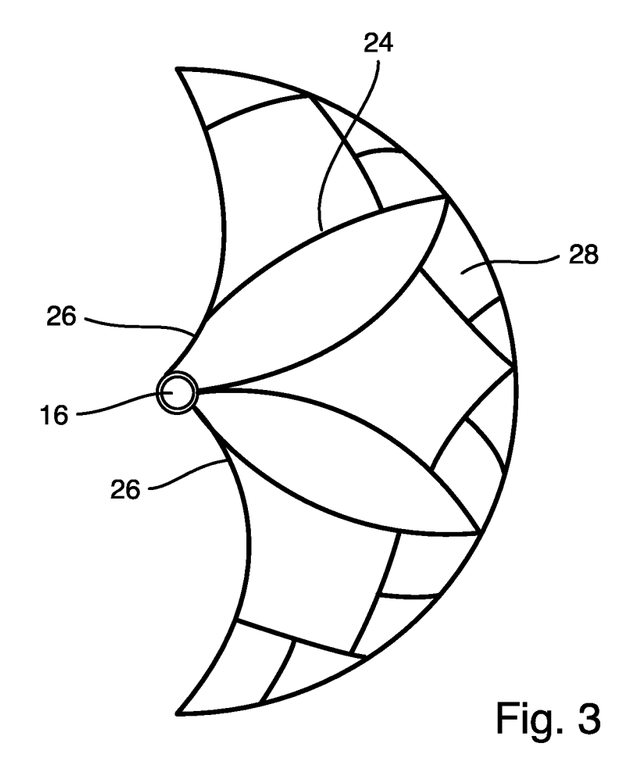
FIG. 3 is a plan view of one half of the occluder according to FIG. 2.

The occluder 12 is initially in its self-expanded shape and thus has a spherical outer contour (cf. FIG. 2). The outer tube 110 is inserted into the occluder 12 through an insertion opening (not shown) in the biological tissue 40 of the occluder 12 and through the tubular proximal tube portion 16. The inner tube 108 is then passed through the occluder 12 and the outer tube 110 and arranged on the distal pot-shaped end portion 18 of the occluder 12. The latching finger-like portions 136 are secured against elastic deformation in the radially inward direction by the inner tube 108, so that the latching fingers 136 come to rest against the proximal tubular portion 16 in a form-fitting manner.

Figure 6:
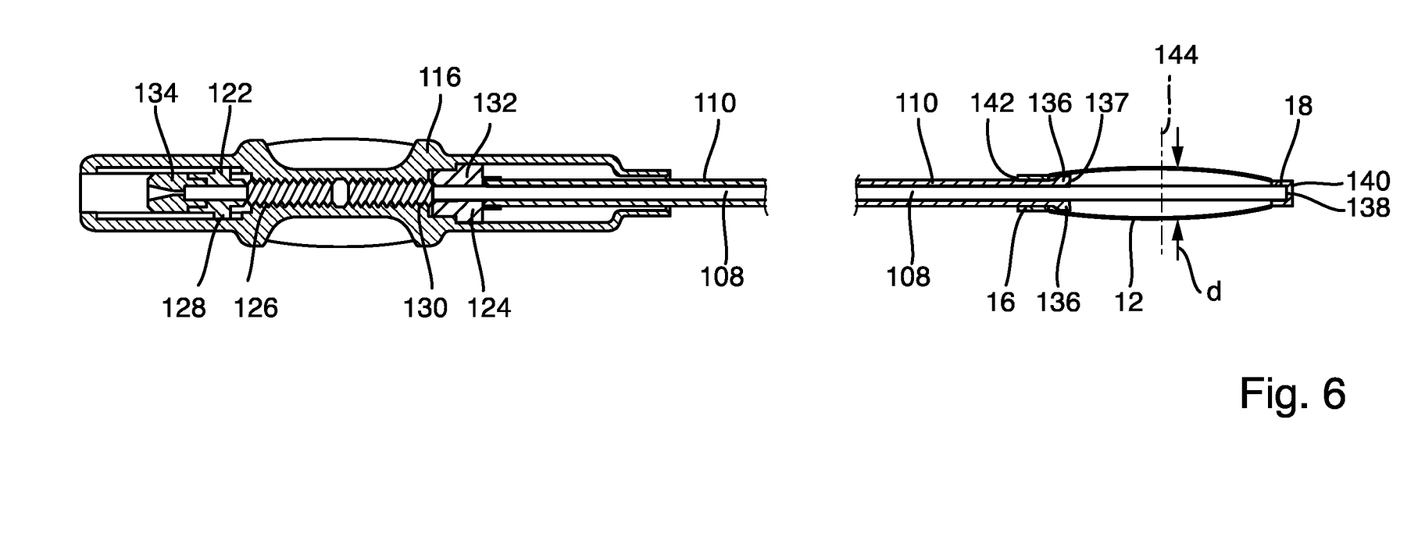
FIG. 6 is a schematic cross-sectional view of the insertion unit according to FIG. 1, with an occluder arranged thereon in the insertion position.

The housing 114 can then be picked up by an operator, in particular a surgeon, and the actuating element 116 can be rotated. As shown in FIG. 6, the actuating element 116 is first rotated in such a way that the head-like portions 128, 132 of the two transmission elements 122, 124 are moved toward one another. As a result, the distal end 137 of the outer tube 110 and the distal end 138 of the inner tube 108 are moved away from one another. As a result, the distal end 140 of the occluder 12 is displaced in the distal direction 29, while the proximal end 142 of the occluder is displaced in the proximal direction 27. Overall, the occluder 12 is in this case transferred into an insertion position, so that the occluder 12 as a whole assumes a compressed form in which it has, by comparison with the self-expanded form, an elongate outer contour having a reduced diameter d (cf. FIG. 6). In this compressed insertion position, the occluder 12 can be inserted into a blood vessel together with the insertion catheter 104 and then brought further up to the left atrial appendage to the intended position. The position of the occluder 12 can be determined by means of the X-ray markers 38. The central region of the occluder 12, i.e. the region of the X-ray markers 38, is intended to come to rest against the left atrial appendage.

Figure 7:
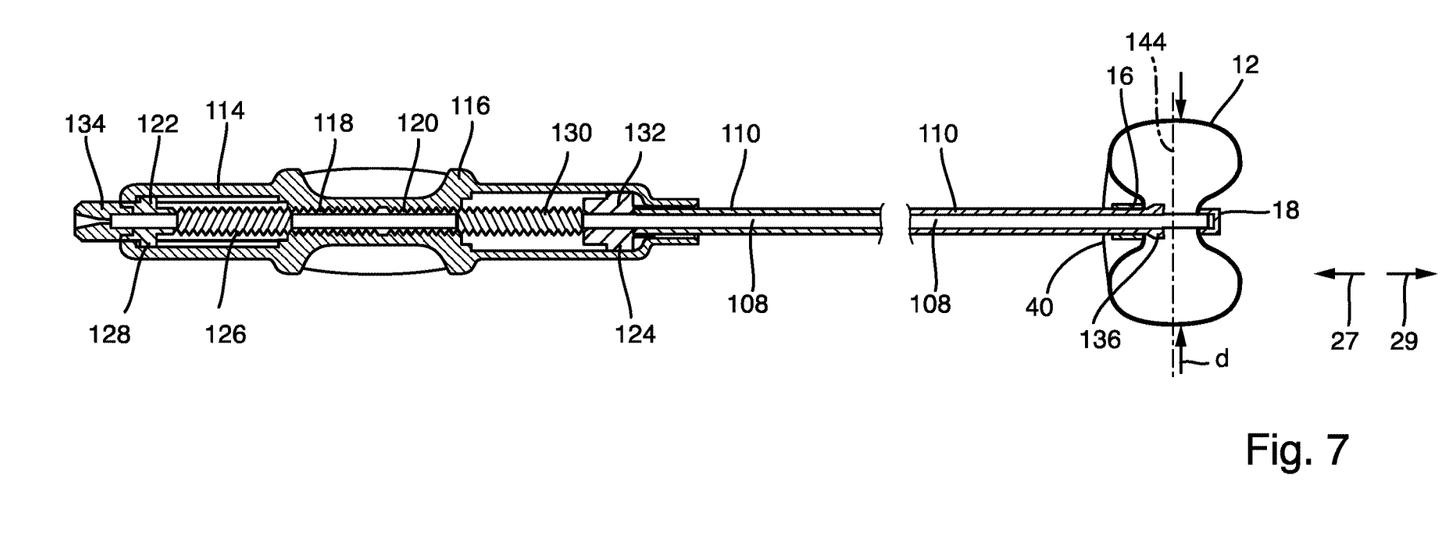
FIG. 7 is a schematic cross section of the insertion unit according to FIG. 1 with the occluder arranged thereon, in a configuration before the insertion unit is removed from the occluder.
Figure 8:
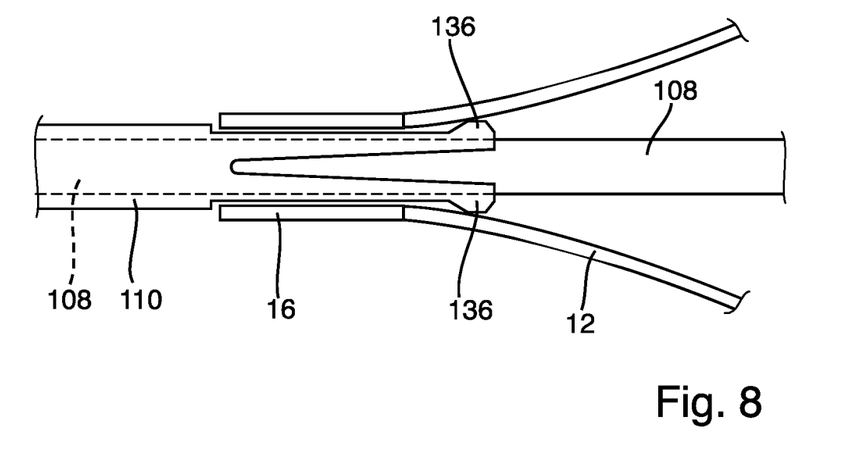
FIG. 8 is a schematic cross section of a region around the proximal end of the occluder, with the insertion unit arranged thereon.

In order to then release the occluder 12, the actuating element 116 is rotated, as shown in FIG. 7, such that the head-like portions 128, 132 are moved away from one another. As a result, the inner tube 108 is moved in the proximal direction 27, while the outer tube 110 is moved in the distal direction 29. In the course of this relative movement, the proximal end 142 of the occluder 12 and the distal end 140 of the occluder 12 are moved toward one another. As a result, the diameter d of the occluder 12 increases. The occluder 12 pushes into its self-expanded shape, so that the proximal end 142 and the distal end 140 of the occluder push toward one another.

In this case, the position of the central part of the occluder 12 remains in particular unchanged, which is shown in FIGS. 6 and 7 with reference to the center line 144. The center line 144 extends through the middle of the occluder 12 between the proximal end 142 and the distal end 140 when said occluder, as shown in FIG. 6, has reached the intended position. The middle of the occluder 12 therefore remains in the correct position and thus does not change position when the occluder is released, as shown in FIG. 7.

In the position shown in FIG. 6, the inner tube 108 is held on the pot-shaped distal end portion 18 of the occluder 12 in a force-fitting manner in the proximal direction 27. Consequently, during a proximal movement of the inner tube 108, the distal end portion 18 of the occluder 12 is also moved in the proximal direction 27. When the occluder 12 is transferred into a position as shown in FIG. 7, the force of the force fit is reduced so that, as shown in FIG. 10, the Luer connector 134 can be detached from the head-like portion 128 with comparatively little effort, so that the Luer connector 134 and thus the inner tube 108 can be pulled off the occluder 12 through the outer tube 110.

Figure 10:
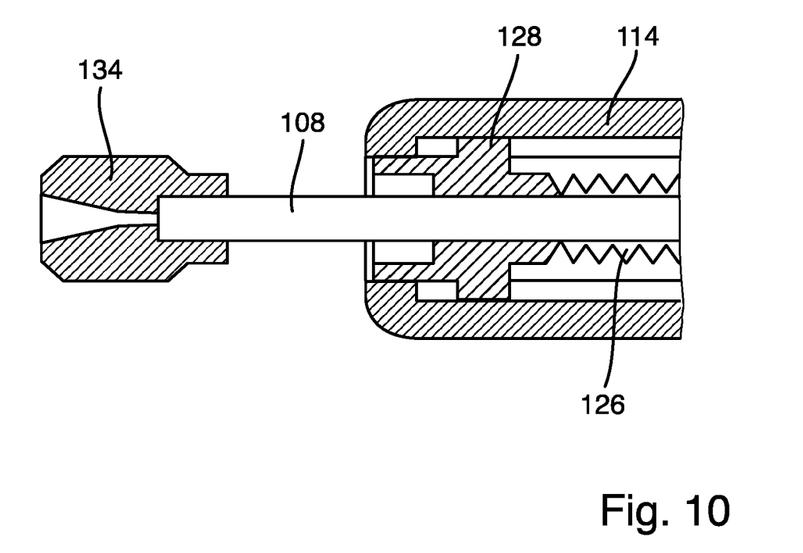
FIG. 10 is a view of a proximal region of the insertion unit with a Luer connector detached from the insertion unit.

Then, as shown in FIG. 10, the outer tube 110 can be pulled off the occluder 12, since the latching finger-like portions 136 can now move elastically radially inward. The occluder 12 can then assume its release position in which it can assume its self-expanded shape, as shown in FIG. 1, or in any case pushes into its self-expanded final shape and thus tightly closes the left atrial appendage. When the insertion catheter has been removed from the occluder 12 after the occluder 12 has been released, the elastically yielding tissue 40 can contract in such a way that the insertion opening (not shown) in the tissue 40 is closed in a substantially fluid-tight manner, so that overall the tissue 40 closes off the proximal hemisphere 32 in a substantially or completely fluid-tight manner and substantially or completely covers the frame 14. The patient's skin can then grow over the biological tissue 40, so that the left atrial appendage can be permanently and stably closed.

As a result of the proposed configuration, the insertion catheter 104 can be pulled off the occluder 12 in a particularly simple manner. This can be achieved in particular without, or almost without, a torque being exerted on the occluder 12. This reduces the risk of the occluder being displaced from its intended position in an undesirable manner when the insertion catheter 104 is pulled off the occluder 12.

What is claimed is:

1. System for inserting a self-expandable occluder into a patient and for releasing the occluder in the left atrial appendage of the patient, the system comprising the occluder, an insertion unit which has a drive unit and has an insertion catheter comprising an outer tube and an inner tube extending through the outer tube, wherein a proximal end region of the occluder is movement-coupled to the outer tube, wherein a distal end region of the occluder is movement-coupled to the inner tube, wherein, in order to release the occluder, the drive unit interacts with the inner tube and the outer tube such that, when actuated, the inner tube can be moved in a distal or proximal direction and the outer tube can be moved in the proximal direction or distal direction, so that the distal end and the proximal end of the occluder can be moved away from or toward one another, characterized in that the drive unit has a first transmission element that has a first transmission thread designed as an external thread, a second transmission element that has a second transmission thread designed as an external thread, and an actuating element that can be actuated by an operator and has a first drive thread designed as an internal thread that interacts with the first transmission thread and a second drive thread designed as an internal thread that interacts with the second transmission thread, wherein the first transmission element is movement-coupled to the inner tube, and wherein the second transmission element is movement-coupled to the outer tube, and in that the first transmission thread and the second transmission thread and the first and the second drive thread are designed such that, when the actuating element is actuated, the inner tube and the outer tube are each moved synchronously in the opposite distal or proximal direction by the same distance.

2. System according to claim 1, wherein the inner tube can be guided by at least one drive thread.

3. System according to claim 1, wherein the outer tube ends in front of the inner tube in the distal direction.

4. System according to claim 1, wherein the occluder comprises a frame having a tubular proximal end portion through which the insertion catheter is inserted into the occluder.

5. System according to claim 1, wherein the occluder comprises a pot-shaped distal end region on which the inner tube of the insertion catheter is arranged.

6. System according to claim 1, wherein, in order to be inserted into a patient, the occluder can be transferred into an insertion position by moving a distal end of the inner tube and a distal end of the outer tube relative to one another and away from one another, so that the proximal end and the distal end of the occluder can be moved away from one another.

7. System according to claim 6, wherein, in order to release the occluder, the distal ends of the inner tube and the outer tube can be moved toward one another such that the proximal end and the distal end of the occluder can be moved toward one another, wherein a central part of the occluder between the proximal end and the distal end keeps its position substantially unchanged during the release of the occluder.

8. System according to claim 1, wherein the outer tube has, at its distal end region, at least one latching finger-like portion which interacts with the proximal end region of the occluder for the purpose of movement coupling.

9. System according to claim 8, wherein the first transmission element interacts with a Luer connector arranged on the inner tube for the purpose of movement coupling to the inner tube.

10. System according to claim 8, wherein the latching finger-like portion interacts with the proximal end region of the occluder in a form-fitting manner when the inner tube is arranged in the occluder.

11. System according to claim 10, wherein, in order to remove the insertion catheter from the occluder, the inner tube can first be pulled out of the occluder, and then the outer tube can be pulled out of the occluder as soon as the inner tube has been pulled out of the occluder through the outer tube.

12. System according to claim 1, wherein the drive unit has a housing which can be held by an operator, and wherein the transmission elements and the actuating element are arranged in or on the housing.

13. System according to claim 12, wherein the actuating element is rotatably arranged on the housing.

14. Insertion unit for a system for inserting a self-expandable occluder into a patient and for releasing the occluder in the left atrial appendage of the patient, the system comprising the occluder, an insertion unit which has a drive unit and has an insertion catheter comprising an outer tube and an inner tube extending through the outer tube, wherein a proximal end region of the occluder is movement-coupled to the outer tube, wherein a distal end region of the occluder is movement-coupled to the inner tube, wherein, in order to release the occluder, the drive unit interacts with the inner tube and the outer tube such that, when actuated, the inner tube can be moved in a distal or proximal direction and the outer tube can be moved in the proximal direction or distal direction, so that the distal end and the proximal end of the occluder can be moved away from or toward one another, characterized in that the drive unit has a first transmission element that has a first transmission thread designed as an external thread, a second transmission element that has a second transmission thread designed as an external thread, and an actuating element that can be actuated by an operator and has a first drive thread designed as an internal thread that interacts with the first transmission thread and a second drive thread designed as an internal thread that interacts with the second transmission thread, wherein the first transmission element is movement-coupled to the inner tube, and wherein the second transmission element is movement-coupled to the outer tube, and in that the first transmission thread and the second transmission thread and the first and the second drive thread are designed such that, when the actuating element is actuated, the inner tube and the outer tube are each moved synchronously in the opposite distal or proximal direction by the same distance.

15. Method for using a system for inserting a self-expandable occluder into a patient and for releasing the occluder in the left atrial appendage of the patient, the system comprising the occluder, an insertion unit which has a drive unit and has an insertion catheter comprising an outer tube and an inner tube extending through the outer tube, wherein a proximal end region of the occluder is movement-coupled to the outer tube, wherein a distal end region of the occluder is movement-coupled to the inner tube, wherein, in order to release the occluder, the drive unit interacts with the inner tube and the outer tube such that, when actuated, the inner tube can be moved in a distal or proximal direction and the outer tube can be moved in the proximal direction or distal direction, so that the distal end and the proximal end of the occluder can be moved away from or toward one another, characterized in that the drive unit has a first transmission element that has a first transmission thread designed as an external thread, a second transmission element that has a second transmission thread designed as an external thread, and an actuating element that can be actuated by an operator and has a first drive thread designed as an internal thread that interacts with the first transmission thread and a second drive thread designed as an internal thread that interacts with the second transmission thread, wherein the first transmission element is movement-coupled to the inner tube, and wherein the second transmission element is movement-coupled to the outer tube, and in that the first transmission thread and the second transmission thread and the first and the second drive thread are designed such that, when the actuating element is actuated, the inner tube and the outer tube are each moved synchronously in the opposite distal or proximal direction by the same distance, comprising the following method steps:
   a. the outer tube is guided through the proximal tubular tube portion, so that at least the latching finger-like portions are inside the occluder;
   b. the inner tube is guided through the outer tube and the occluder up to the distal pot-shaped end portion, so that the latching finger-like portions of the outer tube are secured by the inner tube against radially inward elastic deformation and rest against the tube portion in a form-fitting manner;
   c. the inner tube is moved in the distal direction and the outer tube is moved in the proximal direction so that the occluder is brought into its insertion position;
   d. the occluder is moved within the insertion catheter, in its insertion position, into the region of the left atrial appendage.

16. Method for using a system for inserting a self-expandable occluder into a patient and for releasing the occluder in the left atrial appendage of the patient, the system comprising the occluder, an insertion unit which has a drive unit and has an insertion catheter comprising an outer tube and an inner tube extending through the outer tube, wherein a proximal end region of the occluder is movement-coupled to the outer tube, wherein a distal end region of the occluder is movement-coupled to the inner tube, wherein, in order to release the occluder, the drive unit interacts with the inner tube and the outer tube such that, when actuated, the inner tube can be moved in a distal or proximal direction and the outer tube can be moved in the proximal direction or distal direction, so that the distal end and the proximal end of the occluder can be moved away from or toward one another, characterized in that the drive unit has a first transmission element that has a first transmission thread designed as an external thread, a second transmission element that has a second transmission thread designed as an external thread, and an actuating element that can be actuated by an operator and has a first drive thread designed as an internal thread that interacts with the first transmission thread and a second drive thread designed as an internal thread that interacts with the second transmission thread, wherein the first transmission element is movement-coupled to the inner tube, and wherein the second transmission element is movement-coupled to the outer tube, and in that the first transmission thread and the second transmission thread and the first and the second drive thread are designed such that, when the actuating element is actuated, the inner tube and the outer tube are each moved synchronously in the opposite distal or proximal direction by the same distance, comprising the following method step:

e. the inner tube is moved in the proximal direction and the outer tube is moved in the distal direction, preferably synchronously by the same distance, so that the occluder develops into its self-expanded shape on the left atrial appendage.

17. Method for using a system for inserting a self-expandable occluder into a patient and for releasing the occluder in the left atrial appendage of the patient, the system comprising the occluder, an insertion unit which has a drive unit and has an insertion catheter comprising an outer tube and an inner tube extending through the outer tube, wherein a proximal end region of the occluder is movement-coupled to the outer tube, wherein a distal end region of the occluder is movement-coupled to the inner tube, wherein, in order to release the occluder, the drive unit interacts with the inner tube and the outer tube such that, when actuated, the inner tube can be moved in a distal or proximal direction and the outer tube can be moved in the proximal direction or distal direction, so that the distal end and the proximal end of the occluder can be moved away from or toward one another, characterized in that the drive unit has a first transmission element that has a first transmission thread designed as an external thread, a second transmission element that has a second transmission thread designed as an external thread, and an actuating element that can be actuated by an operator and has a first drive thread designed as an internal thread that interacts with the first transmission thread and a second drive thread designed as an internal thread that interacts with the second transmission thread, wherein the first transmission element is movement-coupled to the inner tube, and wherein the second transmission element is movement-coupled to the outer tube, and in that the first transmission thread and the second transmission thread and the first and the second drive thread are designed such that, when the actuating element is actuated, the inner tube and the outer tube are each moved synchronously in the opposite distal or proximal direction by the same distance, comprising the following method steps:

f. the inner tube is moved in the proximal direction, so that the inner tube is at least in part no longer arranged within the occluder, in particular on the tube portion, wherein the outer tube elastically deforms radially inward and no longer rests against the tube portion in a form-fitting manner;

g. the outer tube is moved in the proximal direction, so that the outer tube is at least no longer arranged on the tube portion;

h. the insertion catheter, the inner tube and the outer tube are removed from the patient simultaneously or one after the other.

\* \* \* \* \*